US009387121B2

(12) United States Patent
Wiljanen et al.

(10) Patent No.: US 9,387,121 B2
(45) Date of Patent: Jul. 12, 2016

(54) INTRAOCULAR IRRIGATOR-ASPIRATOR TIP COMPONENT

(71) Applicant: MicroSurgical Technology, Inc., Redmond, WA (US)

(72) Inventors: Kenneth J. Wiljanen, Seattle, WA (US); Robert May, Redmond, WA (US); Lawrence Laks, Bellevue, WA (US)

(73) Assignee: MicroSurgical Technology, Inc., Redmond, WA (US)

( * ) Notice: Subject to any disclaimer, the term of this patent is extended or adjusted under 35 U.S.C. 154(b) by 0 days.

(21) Appl. No.: 14/856,359

(22) Filed: Sep. 16, 2015

(65) Prior Publication Data

US 2016/0067088 A1    Mar. 10, 2016

Related U.S. Application Data

(63) Continuation of application No. 14/559,649, filed on Dec. 3, 2014, now Pat. No. 9,138,347, which is a continuation of application No. 14/046,777, filed on Oct. 4, 2013, now abandoned.

(60) Provisional application No. 61/759,560, filed on Feb. 1, 2013, provisional application No. 61/710,610, filed on Oct. 5, 2012.

(51) Int. Cl.
*A61M 1/00*     (2006.01)
*A61F 9/007*    (2006.01)

(52) U.S. Cl.
CPC .......... *A61F 9/00736* (2013.01); *A61M 1/0064* (2013.01); *A61M 1/0084* (2013.01)

(58) Field of Classification Search
CPC ............ A61F 9/00736; A61M 1/0064; A61M 1/0084
USPC .......................................................... 604/35
See application file for complete search history.

(56) References Cited

U.S. PATENT DOCUMENTS 4,652,255  A    3/1987  Martinez
5,151,083  A    9/1992  Pichler (Continued)

OTHER PUBLICATIONS

"CapsuleGuard® I/A Handpiece MISC Millennium®/ Other Systems 45," Product No. 85915S, Bausch + Lomb Storz® Ophthalmics, <http://www.storzeye.com /products/35697/Single-Use_instruments/CapsuleGuard-I-A-Handpiece-MICS-Millennium-Other-Systems/85915S.aspx> [retrieved Dec. 3, 2014], at least as early as 2010.

*Primary Examiner* — Jason Flick
(74) *Attorney, Agent, or Firm* — Knobbe, Martens, Olson & Bear, LLP

(57) ABSTRACT

An ophthalmic irrigator-aspirator has a handpiece with aspiration and irrigation openings through its distal end. A tip component connects to the handpiece and has an aspiration cannula. A flexible sleeve has an annular hub for watertight connection to the handpiece or a base portion of the tip. The sleeve has an intermediate portion that forms a channel for an irrigation fluid along the exterior of the cannula to an irrigation port in the sleeve. The distal end portion of the sleeve is sized for a watertight connection over the distal portion of the cannula. Such distal end portion of the sleeve has an aspiration port in communication with the cannula aspiration port. The sleeve proximate, intermediate, and distal portions are integral with each other and are formed of a resilient material that allows the sleeve to be tightly fitted on the handpiece or tip base portion and the cannula.

1 Claim, 11 Drawing Sheets

(56) References Cited

U.S. PATENT DOCUMENTS

| | | | |
|---|---|---|---|
| 5,188,589 A * | 2/1993 | Wypych | A61F 9/00745 604/22 |
| 5,282,786 A | 2/1994 | Ureche | |
| 5,547,473 A | 8/1996 | Peyman | |
| 5,718,677 A | 2/1998 | Capetan | |
| 5,873,851 A * | 2/1999 | Nilsson | A61M 1/0084 604/22 |
| 6,428,501 B1 | 8/2002 | Reynard | |
| 2010/0160851 A1* | 6/2010 | Dimalanta | A61M 1/008 604/22 |

* cited by examiner

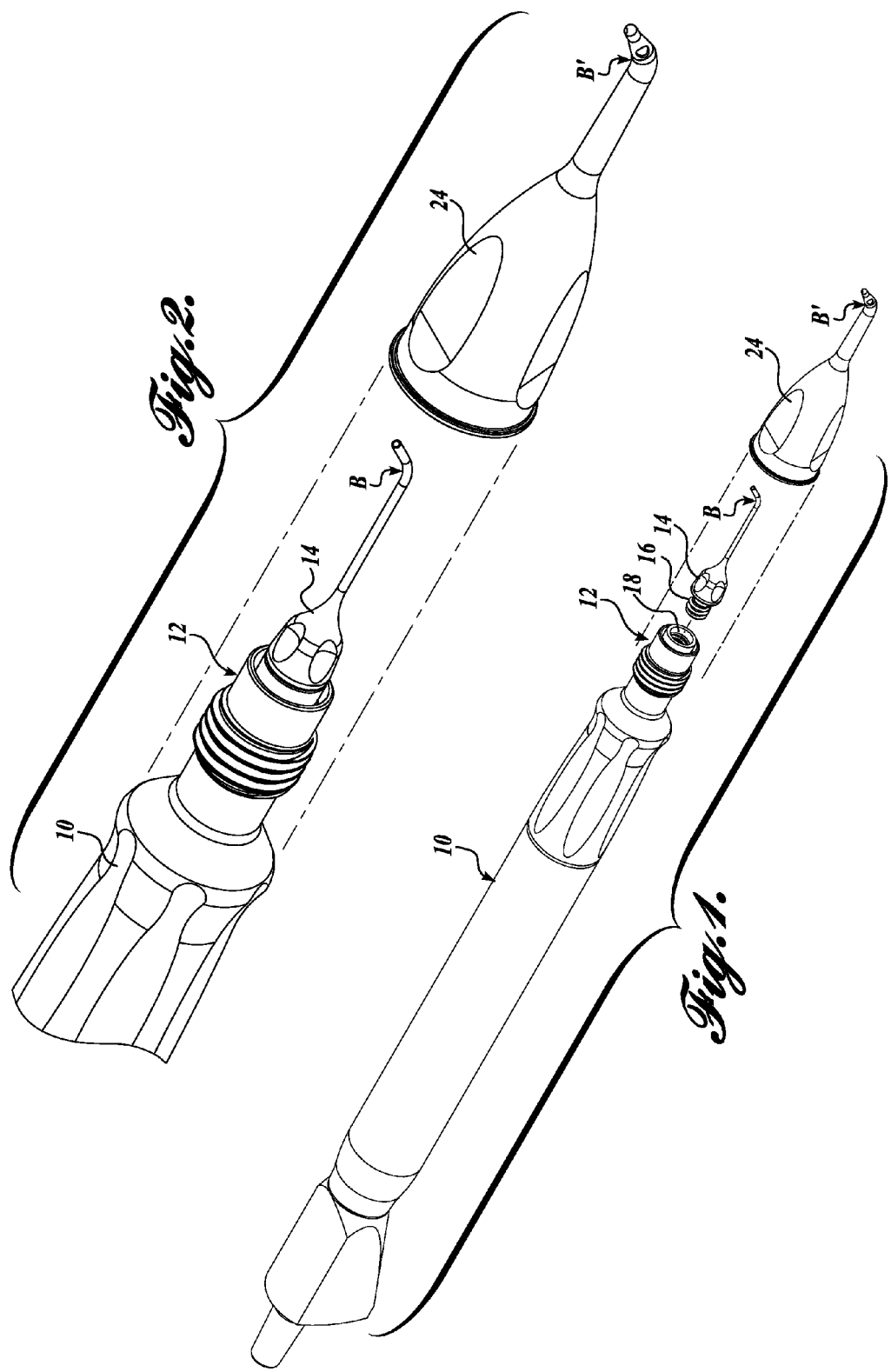

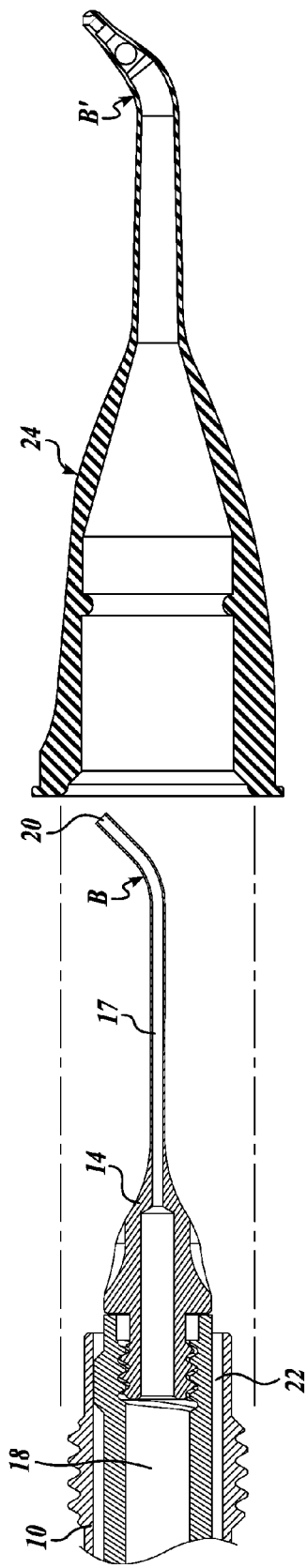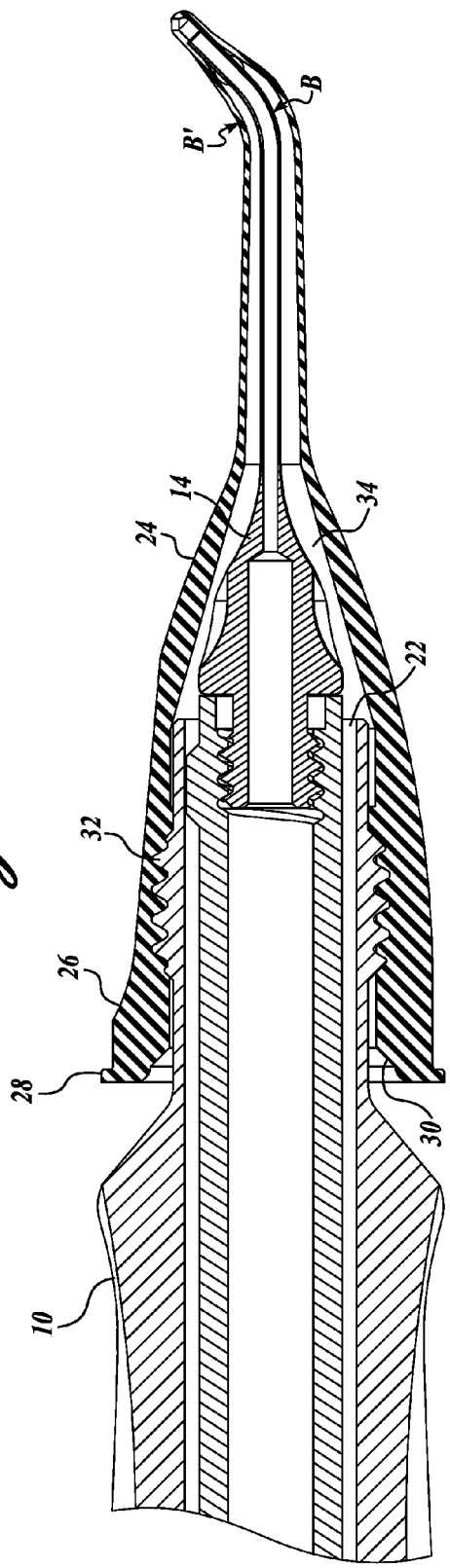
Fig. 3.
Fig. 4.

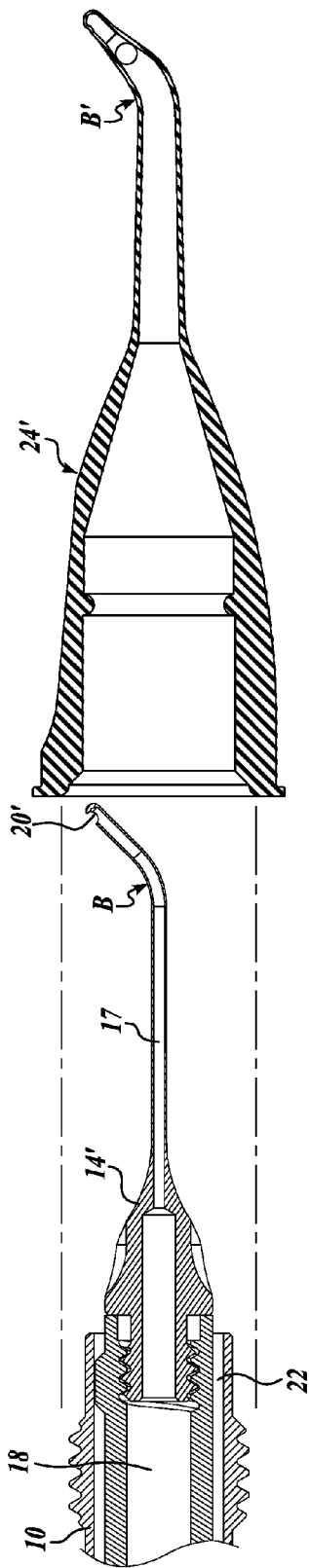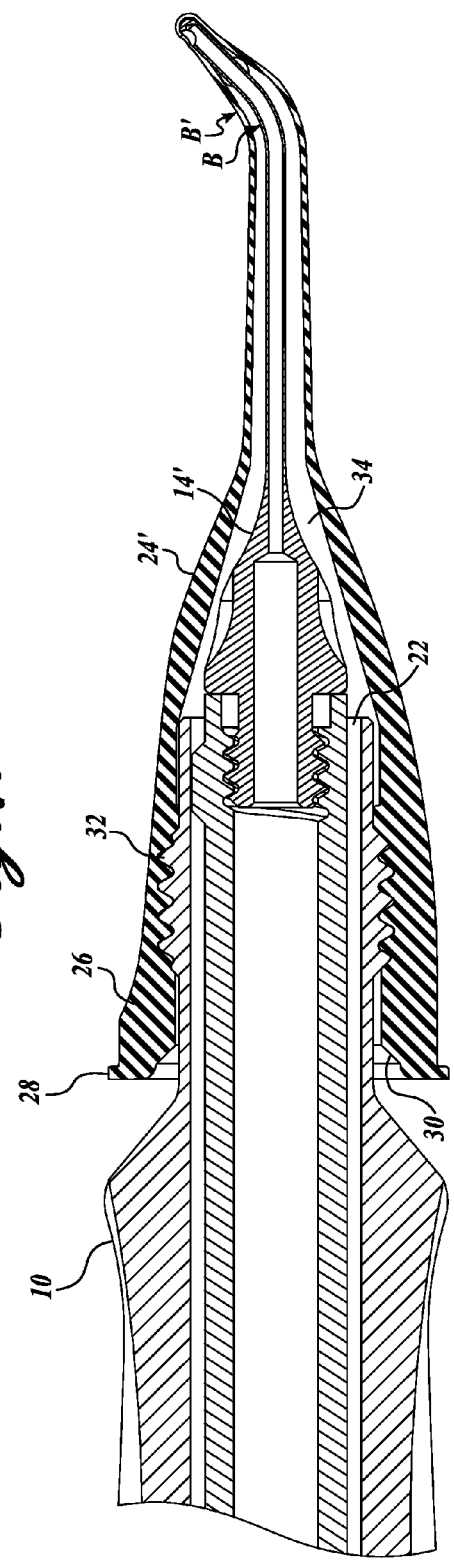
Fig. 7.
Fig. 8.

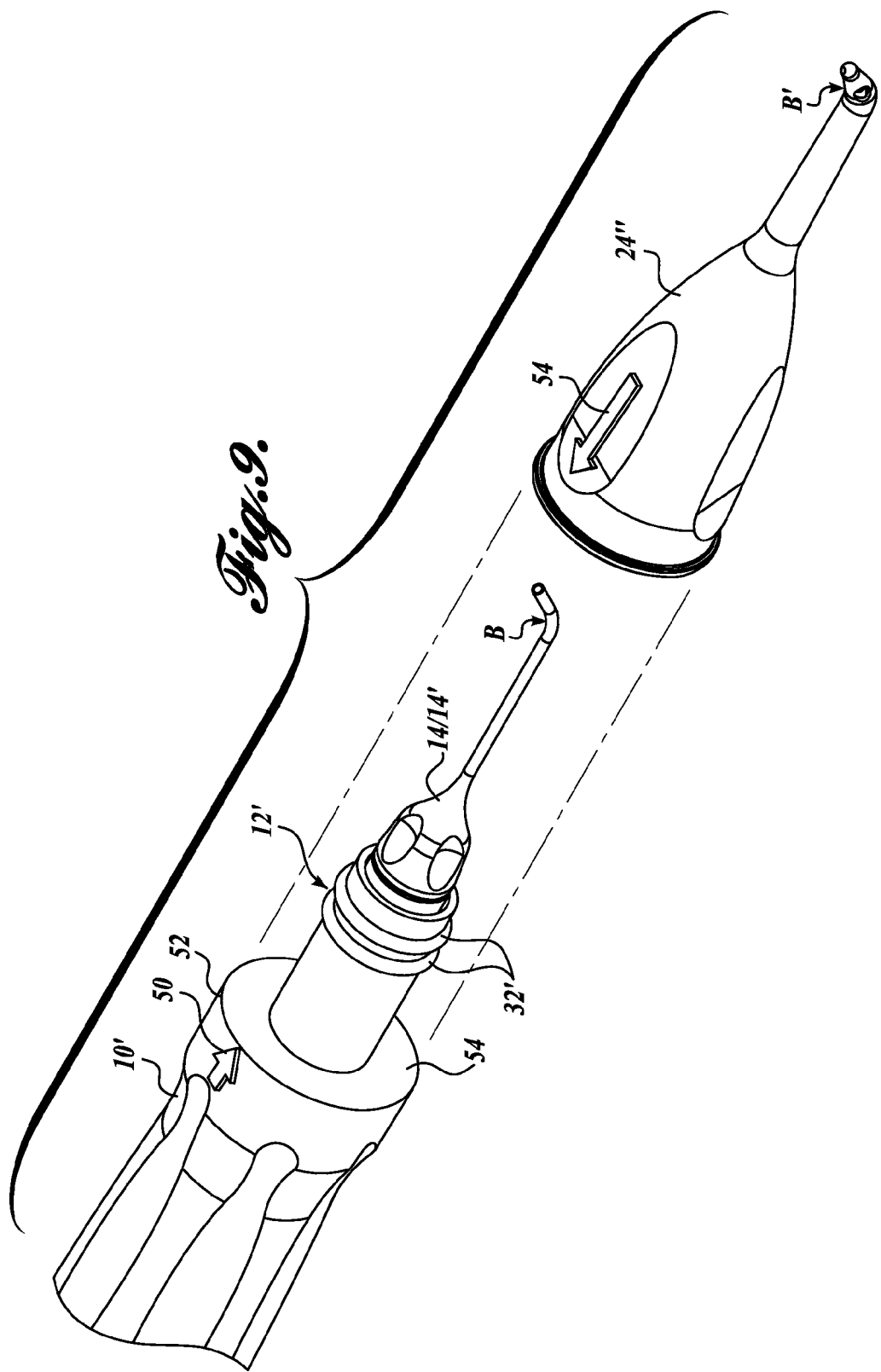

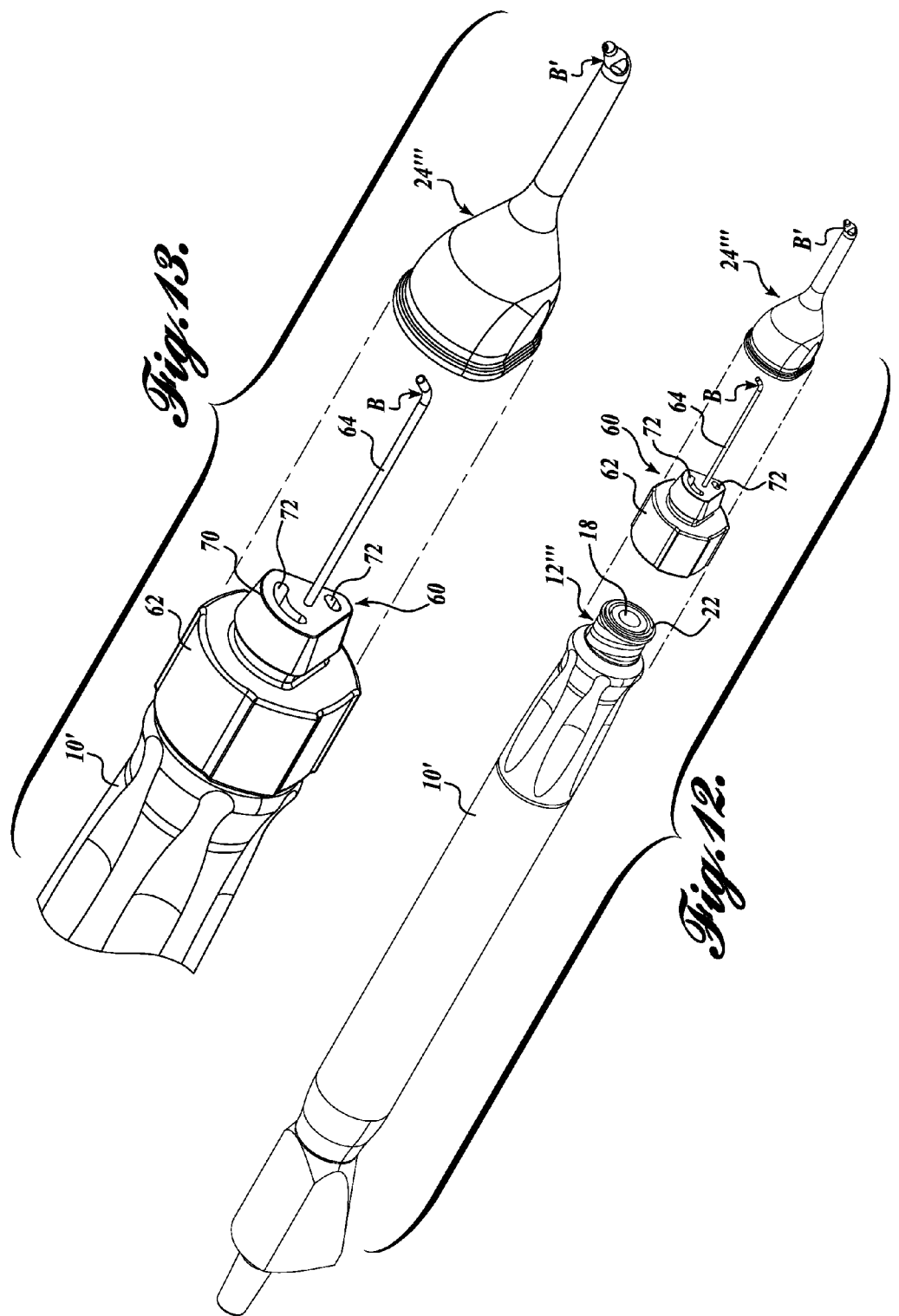

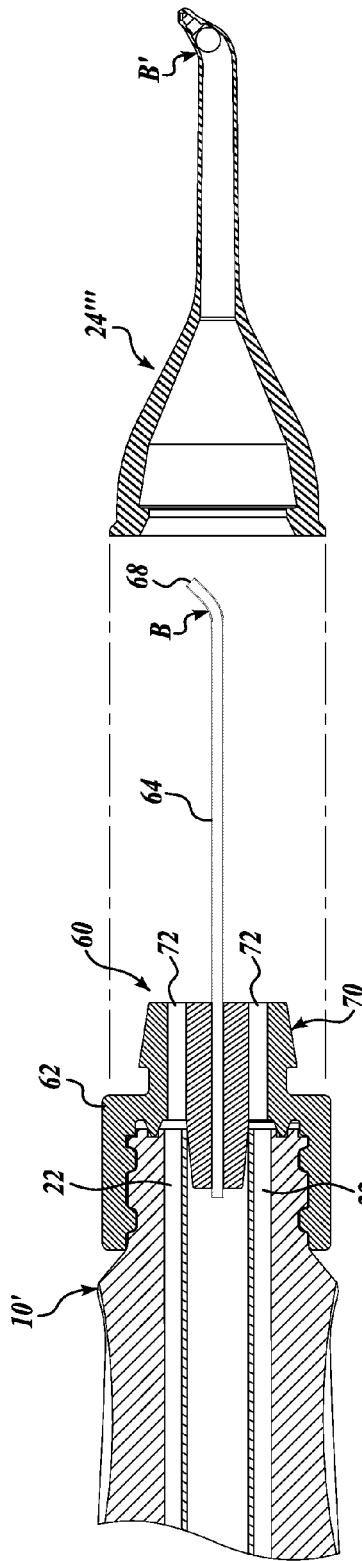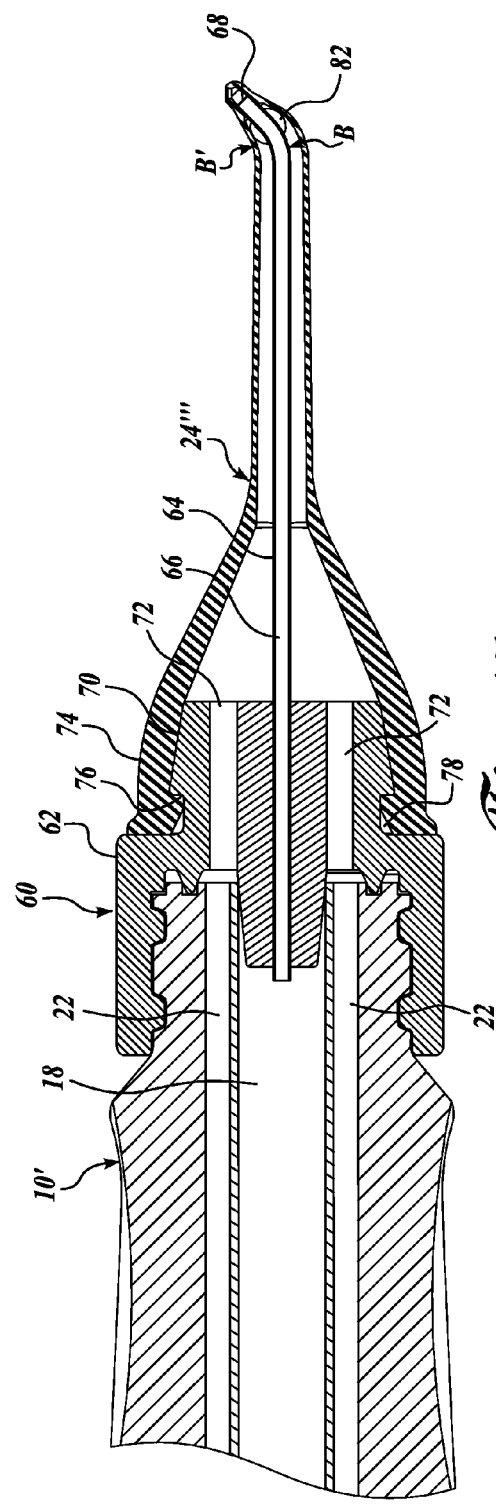

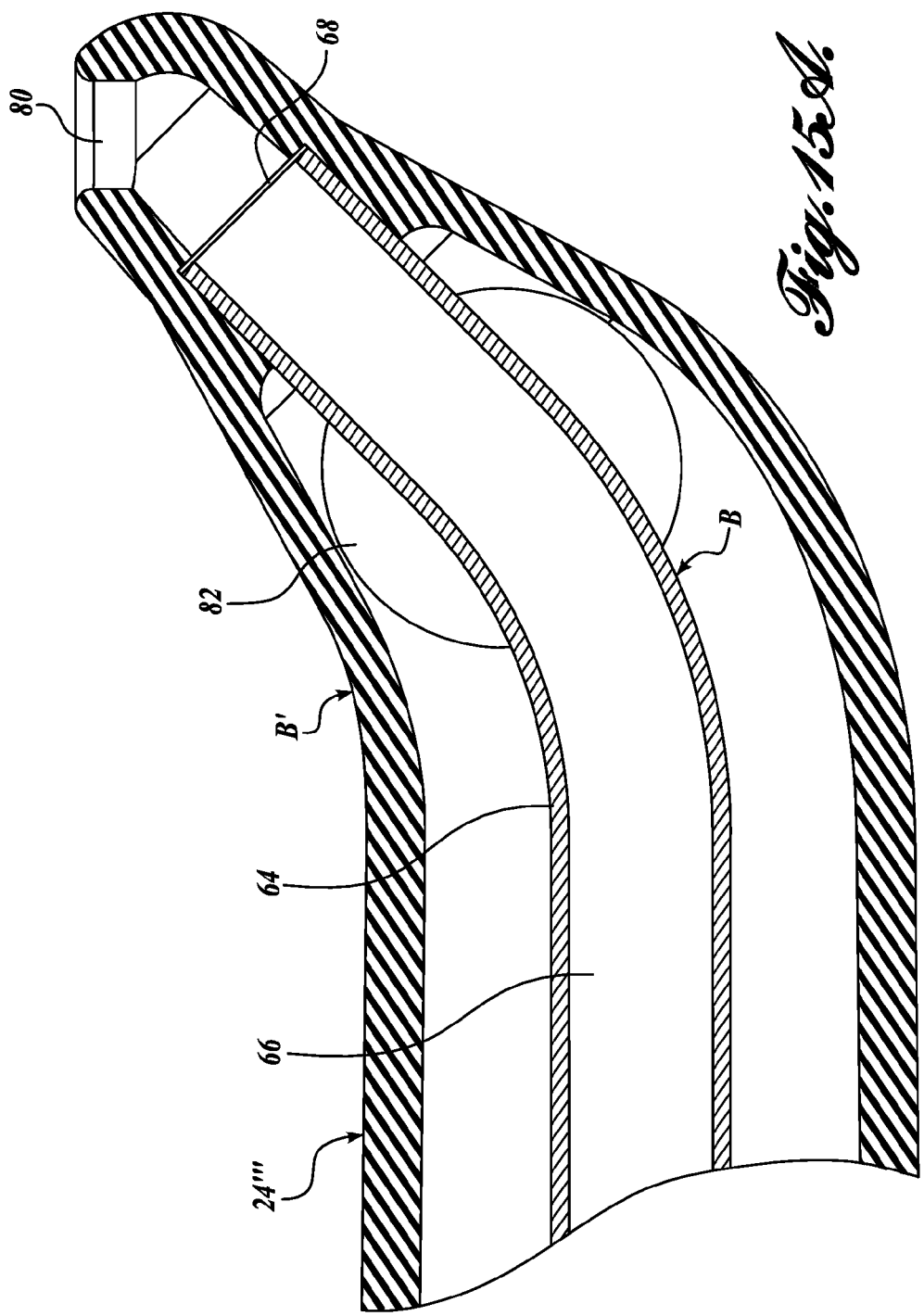

INTRAOCULAR IRRIGATOR-ASPIRATOR TIP COMPONENT

CROSS-REFERENCES TO RELATED APPLICATIONS

This application is a continuation of patent application Ser. No. 14/559,649, filed Dec. 3, 2014, which is a continuation of patent application Ser. No. 14/046,777, filed Oct. 4, 2013, which claims the benefit of Provisional Application No. 61/759,560, filed Feb. 1, 2013, and Provisional Application No. 61/710,610, filed Oct. 5, 2012, the disclosures of which are hereby expressly incorporated by reference herein.

BACKGROUND

The present invention pertains to an improved irrigator-aspirator tip component of the type inserted into the lens capsule of an eye, such as for removing cortical material, washing, cleaning and/or polishing.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In accordance with the present invention, a unitary, one-piece sleeve is provided for an ophthalmic irrigator-aspirator instrument of the type having a handpiece with an aspiration opening through the distal end thereof and one or more irrigation openings adjacent to the aspiration opening. The instrument includes an elongated, narrow tip projecting from the handpiece distal end, such tip having an internal bore communicating with the handpiece aspiration opening and an aspiration port at or adjacent to a distal end of the tip. The novel sleeve has a proximate annular hub portion constructed and arranged to be manually connected to a distal end portion of the handpiece in a watertight fit, with the sleeve surrounding the tip. An intermediate portion of the sleeve forms a channel for an irrigation fluid between the exterior of the tip and the interior portion of the sleeve. The channel is in communication with the handpiece irrigation opening and an irrigation port adjacent to the distal end of the sleeve, for conveying the irrigation fluid through the channel and ejecting it from the irrigation port of the sleeve. The distal end portion of the sleeve is sized for connection over the distal portion of the tip in a watertight fit at a location between the sleeve irrigation port and the aspiration port of the tip. Such distal end portion of the sleeve has an aspiration port located to be in communication with the tip aspiration port. The sleeve proximate, intermediate, and distal portions are integral with each other and are formed of a resilient material that allows the sleeve to be manually stretched onto the handpiece and tip.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1 is a top front perspective of an intraocular irrigator-aspirator tip component in accordance with the present invention with parts shown in exploded relationship;

FIG. 2 is a corresponding perspective thereof on a somewhat larger scale showing some parts assembled;

FIG. 3 is a vertical axial section thereof with the parts shown in the positions of FIG. 2;

FIG. 4 is a section corresponding to FIG. 3 but on a larger scale and with parts fully assembled;

FIG. 4A is a further enlarged, fragmentary, vertical section of the intraocular irrigator-aspirator tip component of FIGS. 1-4;

FIG. 7 is a vertical axial section thereof with the parts shown in the positions of FIG. 6;

FIG. 8 is a section corresponding to FIG. 3 but on a larger scale and with parts fully assembled;

FIG. 9 is a top front perspective of a modified form of an intraocular irrigator-aspirator tip component in accordance with the present invention with parts shown in exploded relationship;

FIG. 12 is a top front perspective of another modified form of an intraocular irrigator-aspirator tip component in accordance with the present invention with parts shown in exploded relationship;

FIG. 13 is a corresponding perspective thereof on a somewhat larger scale showing some parts assembled;

FIG. 14 is a vertical axial section thereof with the parts shown in the positions of FIG. 13;

FIG. 15 is a section corresponding to FIG. 14 but on a larger scale and with parts fully assembled; and FIG. 15A is a further enlarged, fragmentary, vertical section of the intraocular irrigator-aspirator tip component of FIGS. 12-15.

DETAILED DESCRIPTION

Figure 5:
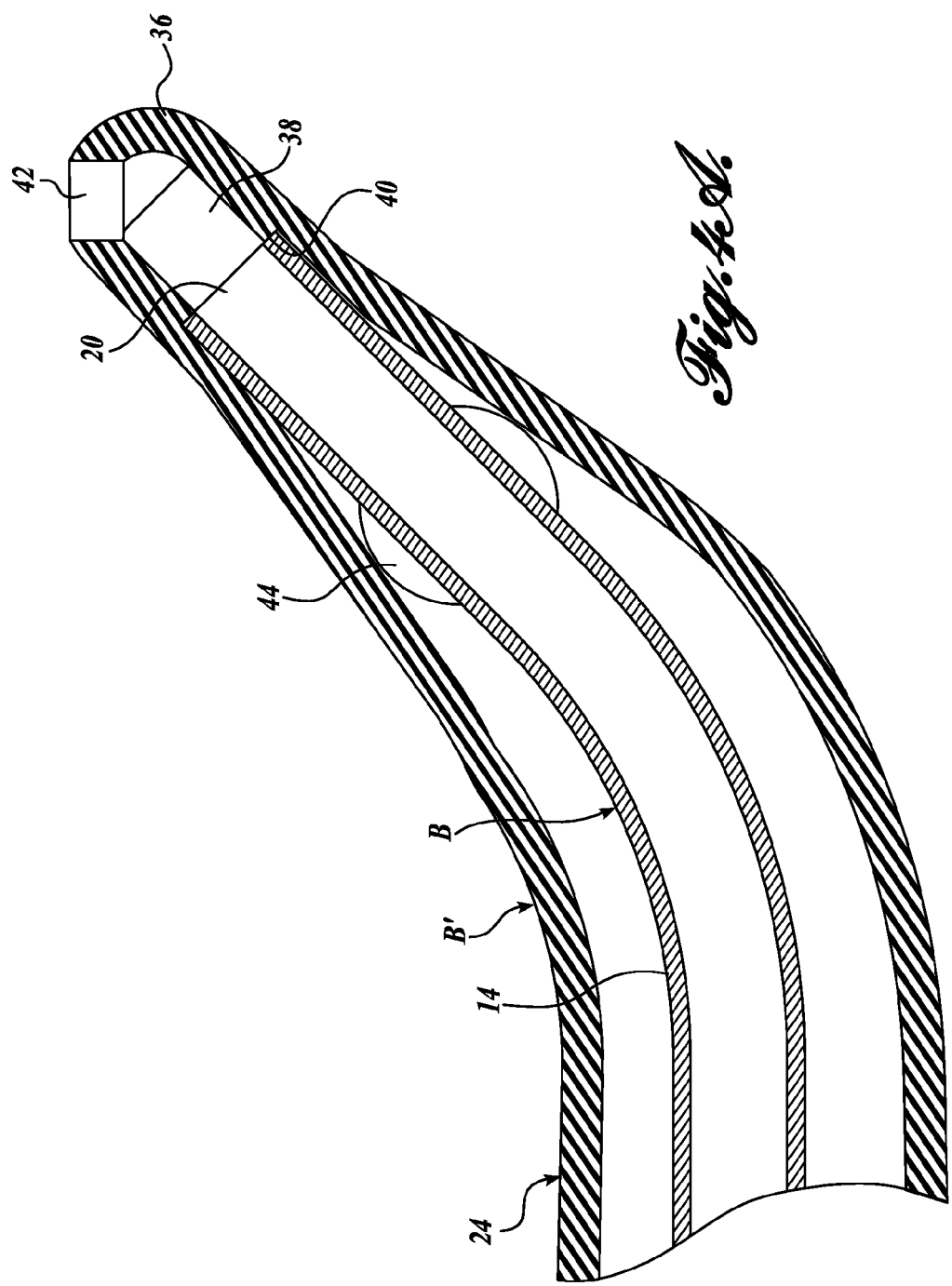
FIG. 5 is a top front perspective of a second embodiment of an intraocular irrigator-aspirator tip component in accordance with the present invention with parts shown in exploded relationship.
Figure 6:
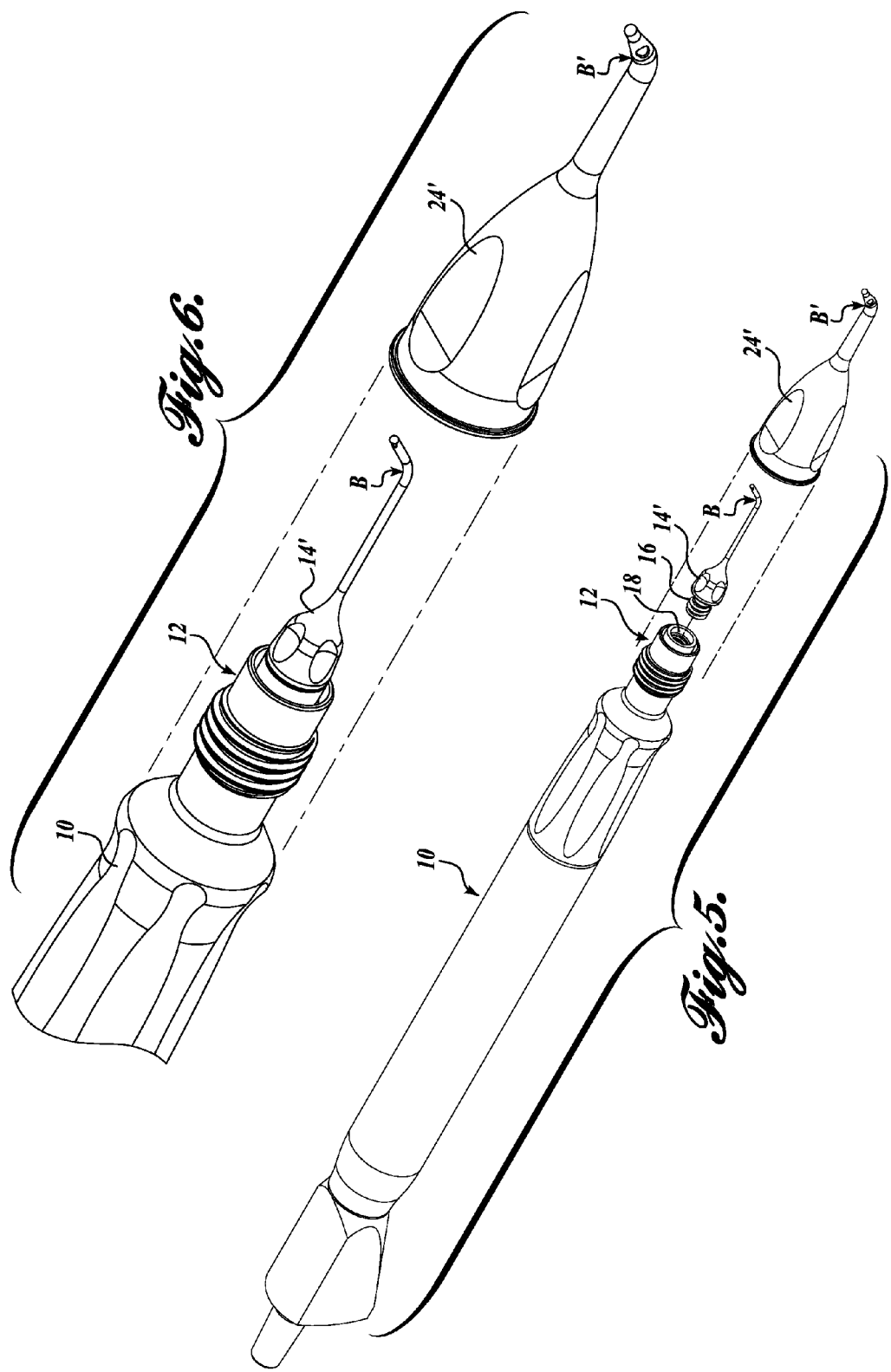
FIG. 6 is a corresponding perspective thereof on a somewhat larger scale showing some parts assembled.

With reference to FIG. 1, an irrigation-aspiration handpiece 10 has a distal portion 12 adapted to receive a separate tip 14 which typically is surgical grade stainless steel or titanium. In a representative embodiment, tip 14 is reusable and has an externally threaded proximate stem 16 for reception in the internally threaded bore 18 that opens at the distal end of the handpiece. FIGS. 2-4 show the tip 14 after it has been joined to the handpiece 10. In FIG. 3 it can be seen that the tip 14 has an internal bore 17 that communicates with the central longitudinal bore 18 of the handpiece 10. At the proximate end, the handpiece is connected to a low pressure or vacuum source, such that aspiration is achieved through the distal end port 20 of the tip 16 as controlled by the user (typically a surgeon). In addition, the handpiece has an annular channel 22 for discharge of an irrigation liquid, such as to compensate for material aspirated through the tip 14.

In accordance with one embodiment of the present invention, a one-piece or unitary sleeve 24 of a soft, resilient material, such as silicone rubber, is provided for fitting tightly over the tip 14 and the distal end portion of the handpiece 10 to which the tip has been joined.

With reference to FIG. 4, the resilient sleeve 24 has a distal hub portion 26 with a wall diameter somewhat greater than the remainder of the sleeve for increased rigidity adjacent to a lip 28 in the area where the sleeve would typically be grasped by the surgeon or technician assembling the apparatus. At the proximate end, on the internal face 30, the sleeve is tapered for ease in fitting the sleeve on and over the distal tip portion of the handpiece. The handpiece can be formed with an external thread 32 or a series of ribs to achieve a watertight fit of the sleeve on the handpiece.

The diameter of an intermediate portion of the sleeve 24 gradually decreases along the length of the tip 14, being sized to form an annular channel 34 which is in communication with the handpiece irrigation channel 22. Moving still farther in a distal direction, the wall thickness of the sleeve lessens to increase the overall flexibility of the sleeve in the area where it will protrude through a corneal incision.

The details of the distal-most portion of the sleeve 24 and inner tip 14 are best seen in FIG. 4A. In this embodiment, the distal end of the tip 14 has the end port 20. The sleeve 24 has a distal end portion 36 that projects beyond the end port 20, with an internal aspiration cavity 38 in communication therewith. In the embodiment shown, the end portion 36 of the sleeve has an annular shoulder 40 to butt against the distal end of the tip 14 when the sleeve is inserted fully over the tip. An external aspiration port 42 is formed in the distal sleeve part 36. In the illustrated embodiment, port 42 extends obliquely, which is preferred, but it can be positioned at any desired location around the sleeve portion 36. The wall thickness at the distal portion 36 is greater than the thickness where the sleeve fits over the tip 14, for a somewhat less flexible but still soft tip that can be manipulated by the surgeon to a desired location. The fit of the sleeve around the distal end of the tip is very snug and watertight.

Still referring to FIG. 4A, one or more ports 44 are provided for expulsion of irrigation liquid close to the aspiration port but nevertheless spaced proximate therefrom. As shown in the drawings, port or ports 44 are located along the distal portion of the tip between the location of a bend B and the aspiration port 20, and the sleeve has a corresponding bend B' at the same location. Thus the distal end portions of the aspiration tip and the sleeve are angled relative to the longer, straight, more proximate portion that extends back toward the handpiece. During an intraocular procedure both ports may be positioned inside the cornea and even inside the lens capsule. The distal part 36 of the sleeve is unsupported and should have sufficient rigidity that it does not collapse so as to block aspiration. Nevertheless, the part of the sleeve 24 proximate to the irrigation port 44 will be fitted through a small corneal slit, and should be sufficiently flexible to conform to the shape of the slit without unduly stretching or tearing the cornea. Whereas the tip 14 itself is very rigid and can have sharp edges that could tear delicate eye tissue with which they come into engagement, the sleeve is soft enough that the risk of tearing, cutting, or abrasion of eye tissue is reduced significantly. In addition, the sleeve protects the tip 14 from being damaged, such as by contact with other instruments during surgery.

FIGS. 5 to 8A correspond, respectively, to FIGS. 1 to 4A, but for a second representative embodiment of the present invention. The handpiece 10 is the same, including the distal portion 12, central aspiration bore 18, and annular irrigation channel 22. The separate tip 14' has the same threaded stem 16 for joining to the handpiece, but the distal end portion of the tip 14' and the distal end portion of the sleeve 24' are a little different.

Figure 8A:
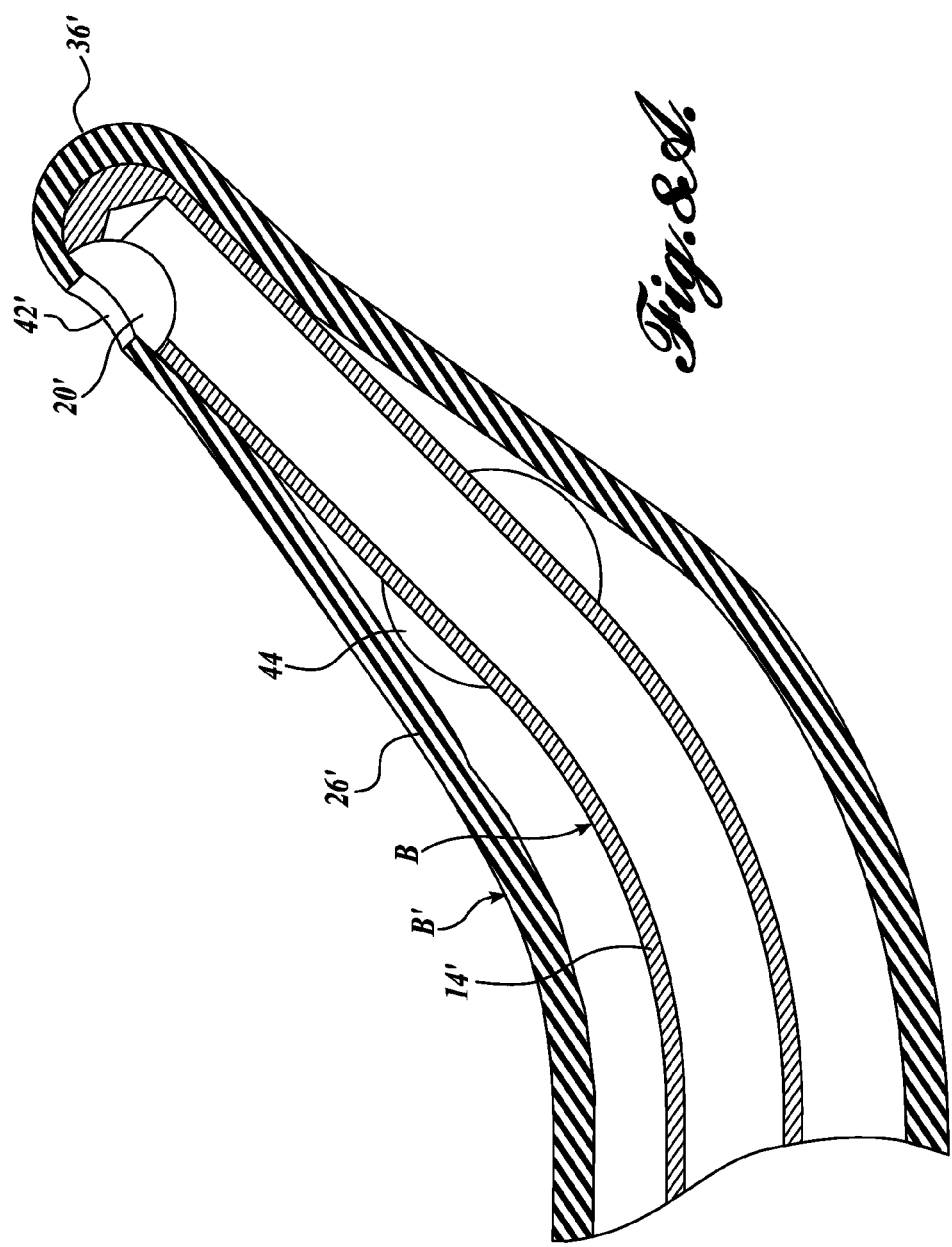
FIG. 8A is a further enlarged, fragmentary, vertical section of the intraocular irrigator-aspirator tip component of FIGS. 5-8.

As best seen in FIG. 8A, the distal end of the tip 14' is closed, and the aspiration port 20' opens through the side, very close to the distal end. The distal end portion 36' of the resilient sleeve tightly embraces the closed end of the tip 14' and the end portion on both sides of the port 20' in a watertight fit. The sleeve 24' has an aspiration port 42' located to register with the tip port 20' when the parts are assembled. Port 42' can be smaller than port 20' so that the hard and potentially sharp metal inner tip will not come in contact with delicate eye tissue during use.

Figure 10:
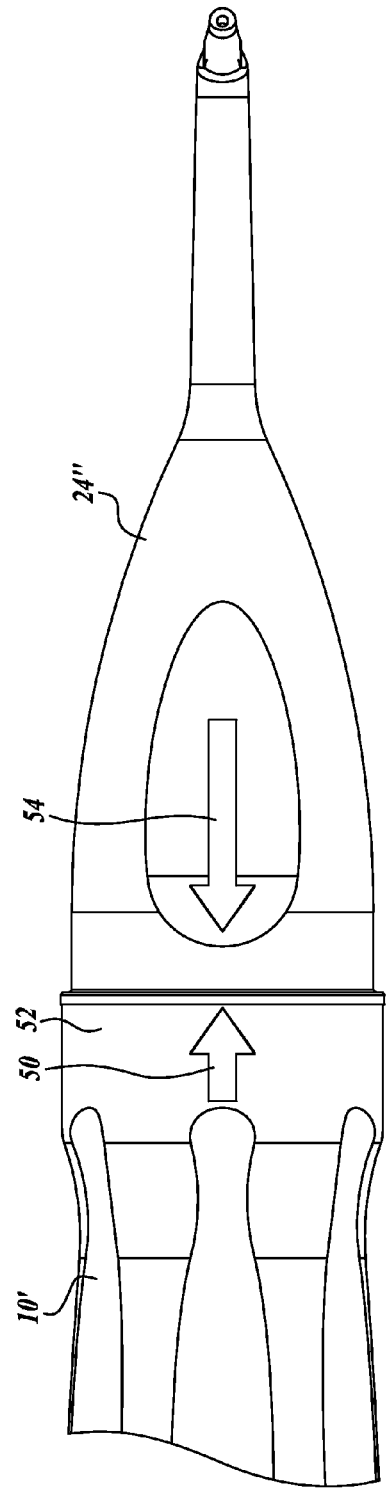
FIG. 10 is a fragmentary, enlarged, top plan thereof with the parts assembled.
Figure 11:
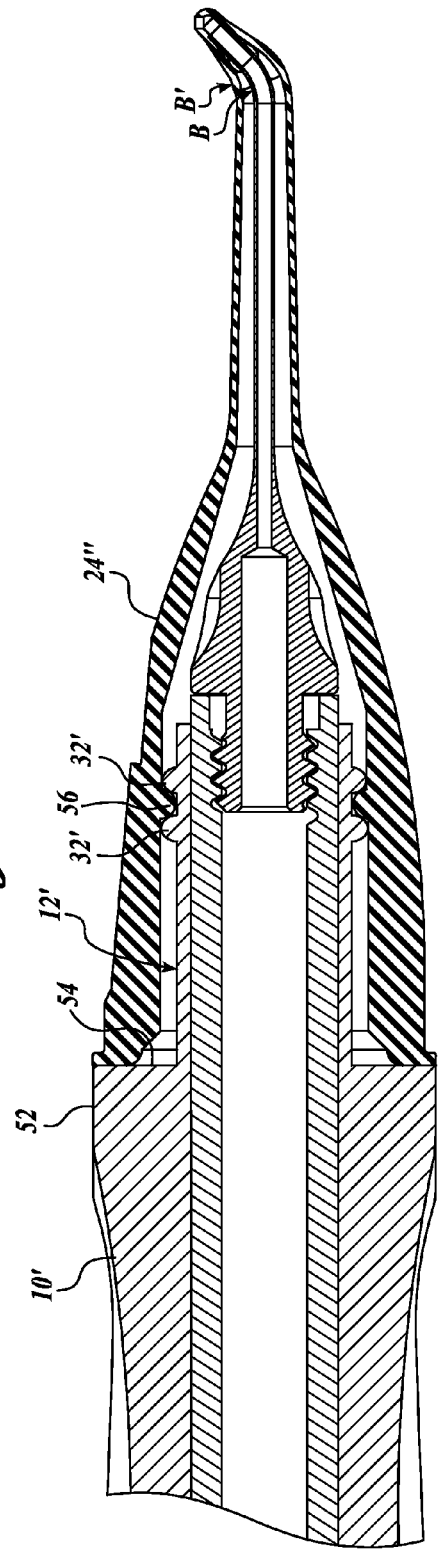
FIG. 11 is a vertical axial section thereof with the parts shown in the positions of FIG. 10.

For both illustrated embodiments it is important that the sleeve 24/24' be fully inserted on the tip 14/14', and for both embodiments it is important that the sleeve be correctly aligned or registered with the tip. FIGS. 9-11 illustrate modifications that can be used with both embodiments to assist in obtaining the correct relative orientation. The tip 14/14' is "clocked" to the handpiece 10' so that the relative orientation will be the same each time one of the aspiration tips is connected. For example, in FIG. 9 the bend B of the tip toward its distal end would always be oriented vertically upward. A registration mark (arrow 50) is formed on the exterior of the handpiece for reference, preferably on an enlarged extension 52. Extension 52 has a flat annular face 54 from which the distal portion 12' extends. Such portion 12' has a pair of longitudinally spaced, circumferential ribs 32' adjacent to the distal end of the handpiece. The sleeve 24" also has a registration mark (arrow 54) formed thereon. During assembly, the surgeon or technical assistant can manually pull the sleeve over the aspirator tip 14/14' while keeping the registration marks in alignment, thereby assuring the correct relative orientation.

In addition, the construction of the modified sleeve 24" and handpiece 10' help assure that the sleeve will be fully stretched over the tip and handpiece to the desired degree, and no more. The proximate end of the sleeve will abut against the face 54 of the handpiece extension 52, and, as seen in FIG. 11, an internal rib 56 of the sleeve 24" is snugly received between the handpiece ribs 32' when the desired fit is achieved.

FIGS. 12 to 15A correspond, respectively, to FIGS. 1 to 4A, but for a third representative embodiment of the present invention. The handpiece 10' is the same as previously described except for the distal portion 12'''. For example, the handpiece of the third embodiment still has the central aspiration bore 18 (see FIGS. 14 and 15) and annular irrigation channel 22, and the bore and channel open through the distal end of the distal portion 12'''. The outer periphery of the distal portion 12''' is configured for connection to a composite rigid tip component 60. Tip component 60 has an internally threaded hub or base 62 for joining to the handpiece, such as by mating threads (external on the handpiece distal portion 12''' and internal in the hub or base 62). FIGS. 13, 14, and 15 show the hub or base 62 connected to the handpiece.

The hub or base 62 can be formed of a rigid plastic material. The composite tip 60 includes a rigid (preferably surgical grade stainless steel or titanium) cannula 64 projecting distally from the hub or base 62. The cannula is fixed in the base, such as by overmolding during manufacturing. As seen in FIG. 15, the bore 66 of the cannula communicates with the aspiration bore 18 of the handpiece and can terminate at or near a distal port 68.

As best seen in FIGS. 13 and 14, the hub or base 62 includes a distal protrusion or stem 70. As seen in FIGS. 14 and 15, stem 70 has longitudinal passages 72 that communicate with the annular irrigation channel 20 of the handpiece.

This embodiment includes a thin-walled resilient sleeve 24''' similar to the sleeves previously described. The proximate end portion (hub) 74 of sleeve 24''' can be fitted tightly over the stem 70 of the composite tip component 60. As best seen in FIG. 15, an interior rib 76 at the proximate end of the sleeve can be received in a groove 78 at the proximate end of the stem for a reliable connection of the sleeve to the stem. For registration purposes, the outer periphery of the stem can be a shape other than cylindrical and the proximate portion of the sleeve shaped the same. In the illustrated embodiment the stem and sleeve are approximately triangular in transverse cross section so the sleeve will be oriented correctly as it is slid on the stem prior to use of the IA instrument.

As best seen in FIG. 15A, the distal end of the rigid cannula opens through an end port 68. The distal end portion of the resilient sleeve 24''' tightly embraces the tip of the cannula in a watertight fit. The sleeve 24''' has an aspiration port 80 in fluid communication with the bore of the cannula, and a nearby irrigation port 82 that communicates with the annular passage for irrigation liquid that flows from the handpiece, such port 82 being positioned between the aspiration end port 68 and the bend B' which overlies the tip bend B, although there can be an overlap of the proximate edge of the irrigation port with the distal part of the tip bend B, as shown in FIG. 15A.

Although this embodiment shows an end port for the cannula, the cannula and sleeve can be modified similar to the embodiment of FIGS. 6 to 8A for a side port application. Either way, it is intended that this embodiment of a composite tip and one-piece or unitary resilient sleeve be sold preassembled as a single use item for quick and reliable connection to a reusable handpiece. Both aspiration and irrigation are supported, and sterility is assured because the tip and sleeve are discarded after one use.

While illustrative embodiments have been illustrated and described, it will be appreciated that various changes can be made therein without departing from the spirit and scope of the invention.

The embodiments of the invention in which an exclusive property or privilege is claimed are defined as follows:

1. An ophthalmic irrigator-aspirator instrument comprising:
a handpiece with proximate and distal ends, the handpiece having an aspiration opening through the distal end thereof and one or more irrigation openings adjacent to the aspiration opening;
a tip component having:
a proximate base portion constructed and arranged to be manually connected to a distal end portion of the handpiece in a watertight fit and surrounding the aspiration and irrigation openings of the handpiece, the base portion having irrigation openings therethrough in communication with the handpiece irrigation openings;
an elongated cannula having a proximate end portion joined to the base portion, a distal end portion, and a bend between the proximate and distal end portions and adjacent to a distal end of the cannula, the cannula having an internal bore communicating with the handpiece aspiration opening and an aspiration port at or adjacent to the distal end of the cannula spaced in a distal direction from the bend; and
a sleeve component having:
a proximate annular hub portion constructed and arranged to be manually connected to a distal end portion of the tip component base portion in a watertight fit;
an intermediate portion surrounding the elongated tip of the instrument and forming an irrigation channel between the tip base portion and an interior portion of the sleeve which channel is in communication with the handpiece irrigation opening, the intermediate sleeve portion having a bend overlying the bend of the cannula, an irrigation port adjacent to a distal end of the sleeve and located at least partially distal to the bend of the elongated tip for ejection of an irrigation fluid therefrom; and
a distal end portion sized for connection over a distal portion of the cannula in a watertight fit at a location distal of the sleeve irrigation port but proximate of the cannula aspiration port, the sleeve distal end portion having an aspiration port located to be in communication with the cannula aspiration port when the sleeve is stretched over the distal portion of the cannula, the sleeve proximate, intermediate, and distal portions being integral with each other and formed of a resilient material that allows the sleeve to be stretched onto the handpiece and tip.

* * * * *